United States Patent
Jankowski et al.

(10) Patent No.: US 11,383,010 B2
(45) Date of Patent: Jul. 12, 2022

(54) METHOD OF DIALYSIS FOR REMOVING PROTEIN-BOUND TOXINS FROM THE BLOOD OF PATIENTS USING HIGH-FREQUENCY ELECTROMAGNETIC FIELDS

(75) Inventors: Joachim Jankowski, Stahnsdorf (DE); Walter Zidek, Berlin (DE); Falko Brettschneider, Berlin (DE); Vera Jankowski, Stahnsdorf (DE)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 545 days.

(21) Appl. No.: 14/130,989

(22) PCT Filed: Jun. 29, 2012

(86) PCT No.: PCT/EP2012/062657
§ 371 (c)(1),
(2), (4) Date: May 2, 2014

(87) PCT Pub. No.: WO2013/004604
PCT Pub. Date: Jan. 10, 2013

(65) Prior Publication Data
US 2014/0246367 A1 Sep. 4, 2014

(30) Foreign Application Priority Data
Jul. 5, 2011 (DE) .................... 10 2011 078 695.3

(51) Int. Cl.
*A61M 1/14* (2006.01)
*A61M 1/16* (2006.01)
(Continued)

(52) U.S. Cl.
CPC ............... *A61M 1/14* (2013.01); *A61M 1/16* (2013.01); *A61M 1/1605* (2014.02);
(Continued)

(58) Field of Classification Search
CPC ........ A61M 1/14; A61M 1/3681; A61M 1/16; A61M 1/1601; A61M 1/3618;
(Continued)

(56) References Cited

U.S. PATENT DOCUMENTS 3,484,369 A * 12/1969 De Dobbeleer .... A61M 1/1668
210/321.65
4,611,599 A * 9/1986 Bentall .................... A61N 1/40
607/27
(Continued)

FOREIGN PATENT DOCUMENTS

DE 2731744 2/1979
DE 3720665 1/1989
(Continued)

OTHER PUBLICATIONS

European Commission, Health and electromagnetic fields, 2005, Research Directorate-General.*
(Continued)

*Primary Examiner* — Joseph W Drodge
(74) *Attorney, Agent, or Firm* — K&L Gates LLP

(57) ABSTRACT

The present invention relates to the use of a high-frequency electromagnetic field in method of dialysis where a dialyser is used for the exchange of substances, wherein the blood to be cleaned is exposed to a high-frequency electromagnetic field prior to and/or during contact with the dialyser, and to a dialysis machine for carrying out the use.

20 Claims, 3 Drawing Sheets

Figure 1:
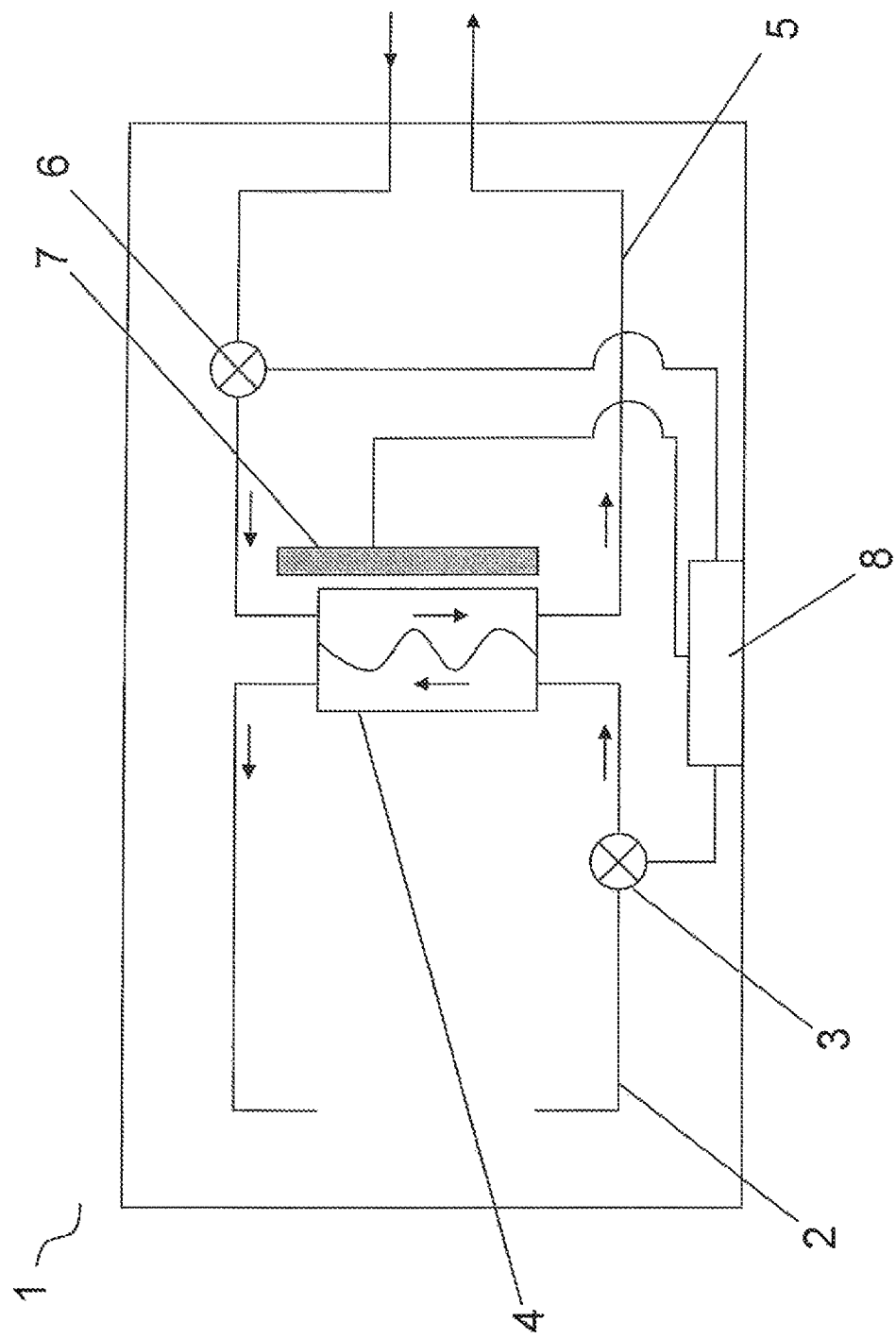

(51) Int. Cl.
 *B01D 61/30* (2006.01)
 *A61M 1/36* (2006.01)
(52) U.S. Cl.
 CPC .......... *A61M 1/3681* (2013.01); *B01D 61/30* (2013.01); *A61M 2205/50* (2013.01)
(58) Field of Classification Search
 CPC .. A61M 1/3621; A61M 1/3653; A61M 1/367; A61M 2205/0272; A61M 1/1605; A61M 1/3403; A61M 1/3434; A61M 1/361; A61M 1/3612; A61M 1/3639; A61M 2202/0014; A61M 2202/0445; A61M 2202/0498; A61M 2205/054; A61M 2205/50; C02F 1/48; C02F 1/487; C02F 2201/48; B01D 17/12; B01D 61/24; B01D 61/30; B01D 61/32; B01D 2311/2684
 USPC ............................ 210/223, 222, 167.29, 695
 See application file for complete search history.

(56) References Cited

U.S. PATENT DOCUMENTS

| | | | | |
|---|---|---|---|---|
| 4,663,006 | A * | 5/1987 | Yao | A61M 1/1696 204/DIG. 9 |
| 4,923,598 | A * | 5/1990 | Schal | A61M 1/16 210/137 |
| 4,963,268 | A * | 10/1990 | Morse | C02F 1/487 204/156 |
| 5,019,076 | A * | 5/1991 | Yamanashi | A61B 18/18 606/49 |
| 5,139,675 | A * | 8/1992 | Arnold | A61L 2/18 134/1 |
| 5,261,874 | A * | 11/1993 | Castle | A61B 5/14557 604/28 |
| 5,980,479 | A * | 11/1999 | Kutushov | A61M 1/36 435/174 |
| 6,042,347 | A * | 3/2000 | Scholl | A61M 60/422 417/423.12 |
| 6,156,007 | A | 12/2000 | Ash | |
| 7,867,214 | B2 | 1/2011 | Childers et al. | |
| 7,935,906 | B2 | 5/2011 | Kibar et al. | |
| 10,172,994 | B2 * | 1/2019 | Tschulena | A61M 1/3434 |
| 10,525,187 | B2 * | 1/2020 | Tschulena | A61M 1/3472 |
| 2003/0004411 | A1 * | 1/2003 | Govari | A61B 17/1114 600/424 |
| 2003/0120197 | A1 * | 6/2003 | Kaneko | A61L 29/18 977/960 |
| 2003/0144721 | A1 * | 7/2003 | Villaseca | A61N 1/056 607/122 |
| 2003/0153024 | A1 | 8/2003 | Sullivan | |
| 2003/0187380 | A1 | 10/2003 | Botto | |
| 2003/0231294 | A1 * | 12/2003 | Wariar | C12Q 1/34 356/39 |
| 2005/0015040 | A1 * | 1/2005 | Wuepper | A61M 1/3681 604/5.01 |
| 2005/0027192 | A1 * | 2/2005 | Govari | A61B 5/6846 600/424 |
| 2005/0082225 | A1 | 4/2005 | Kreymann | |
| 2007/0221577 | A1 * | 9/2007 | Vallee | C02F 1/48 210/695 |
| 2009/0012655 | A1 * | 1/2009 | Kienman | A61M 1/28 700/300 |
| 2009/0082614 | A1 * | 3/2009 | Feucht | A61N 1/40 600/14 |
| 2009/0012087 | A1 | 5/2009 | Kreymann | |
| 2010/0096329 | A1 * | 4/2010 | Kotanko | A61M 1/16 210/749 |
| 2011/0132838 | A1 * | 6/2011 | Curtis | A61M 1/1647 210/133 |
| 2013/0001422 | A1 * | 1/2013 | Lavon | A61M 1/3434 |
| 2013/0240361 | A1 * | 9/2013 | Simonis | A61M 1/3482 204/647 |
| 2015/0306298 | A1 | 10/2015 | Tschulena | |
| 2015/0335811 | A1 | 11/2015 | Jankowski et al. | |

FOREIGN PATENT DOCUMENTS

| | | |
|---|---|---|
| DE | 19651355 | 6/1998 |
| DE | 10321099 | 11/2004 |
| DE | 102008050849 | 4/2010 |
| DE | 102009011901 | 9/2010 |
| DE | 102010028902 | 11/2011 |
| EP | 1362605 | 11/2003 |
| FR | 2087416 | 12/1971 |
| RO | 122077 | 12/2008 |
| WO | 03020403 | 3/2003 |

OTHER PUBLICATIONS

Clinical Mass Spectrometry, "Mass spectrometry in uremia", 1995, Elsevier, SSDI 0009-8981 (95) 06188-J. (Year: 1995).*
Grainger, QuickTips Technical Resources #344: Electric and Magnetic Fields (EMF), Jan. 1, 2012. (Year: 2012).*
John F. Patzer et al, "Voltage Polarity Relay-Optimal Control of Electrochemical Urea Oxidation", published in IEEE Transactions o Biomedical Engineering, vol. 38, Issue No. 11, Nov. 1991. (Year: 1991).*
International Search Report and Written Opinion dated Oct. 26, 2012 in PCT Application No. PCT/EP2012/062657. (7 pages).
International Search Report dated Apr. 15, 2014 in PCT/EP2014/050080.

* cited by examiner

METHOD OF DIALYSIS FOR REMOVING PROTEIN-BOUND TOXINS FROM THE BLOOD OF PATIENTS USING HIGH-FREQUENCY ELECTROMAGNETIC FIELDS

CROSS-REFERENCE TO RELATED APPLICATIONS

This application is a § 371 national stage entry of International Application No. PCT/EP2012/062657, filed Jun. 29, 2012, which claims priority to German Patent Application No. 10 2011 078 695.3, filed Jul. 5, 2011, the contents of both of which are hereby incorporated by reference.

The primary function of the kidneys is to excrete substances that are normally eliminated with the urine, the so-called uraemic toxins. The kidneys of patients suffering from chronic renal failure are no longer able to fulfil this function, which, if untreated, results in poisoning and death of the patient within a short time. Dialysis is the instrument of choice used to alleviate the acute and chronic disease and to bridge the gap until, a suitable donor organ is available. Dialysis is based on the principle of an exchange of substances by means of filtration or diffusion. The membranes used at present act as mere filtration and/or diffusion membranes, ensuring that substances up to a defined maximum size are removed from the blood to be cleaned. Dialysis membranes commonly used today have an exclusion limit of for example, 14,000-17,000 Da. However, the methods of dialysis used at present do, as a rule, not achieve a complete separation of uraemic toxins since part of the substances that are normally eliminated with the urine are bound to proteins. These are, among others, low-molecular aromatic substances. Uraemic toxins that, as a rule, may be bound to proteins include, for example, phenylacetic acid, p-hydroxyhippuric acid and indoxyl sulphate. Consequently, the aforesaid substances accumulate in the organism of the patient, causing secondary diseases related to acute and chronic renal failure. As a result, patients suffering from chronic renal failure increasingly develop secondary diseases, such as cardiovascular disease, leading to an increased mortality rate. For example, dialysis accelerates the development of atherosclerosis. Vascular diseases, such as atherosclerosis, cause the greatest number of deaths in this group of patients.

One reason for this are low-molecular, hydrophobic and aromatic uraemic toxins. Aromatic, hydrophobic uraemic toxins have a low solubility in water. This brings about adsorptive effects between these substances and plasma proteins in most cases. Said adsorptive effects are caused by various types of interaction. These include, above all, hydrogen bridge bonds, ionic bonding and dipole-dipole interaction (van der Waals forces). If the substances that are normally eliminated with the urine are bound to plasma proteins, such as albumin, their effective molecular weight may increase to such an extent that molecular weights much higher than 17,000 Da are reached. As a result, the molecular weight of the protein-bound uraemic toxins is above the exclusion limit of the dialysis membranes used, preventing effective removal of said toxins during dialysis.

As a consequence, only the portion of the relevant uraemic toxin that is not bound to proteins can be separated. The protein-bound portion (up to 95% of the total amount of the uraemic toxin) remains essentially unchanged. Due to the equilibrium according to the law of mass action between uraemic toxins that are bound to proteins and those that are not, the initial concentrations of uraemic toxins that are not bound to proteins are reached again in the plasma of patients suffering from chronic renal failure immediately after dialysis. As the pathophysiological and pathochemical effects are mainly caused by uraemic toxins not bound to proteins, the fact that said equilibrium is re-established initiates a fatal process for the patient. This vicious circle is the underlying cause of the numerous pathological manifestations of chronic renal failure. Up to date, there are no conventional methods by means of which protein-bound uraemic toxins can effectively be removed from the blood to be cleaned during dialysis.

The object of the present invention is to reduce or to avoid at least one drawback of the state of the art described above. In particular, it is an object of the invention to provide means and ways for effectively removing protein-bound uraemic toxins from the blood of dialysis patients.

This object is achieved by making use of a high-frequency electromagnetic field in a method of dialysis where a dialyser is used for the exchange of substances, in particular for haemodialysis or haemofiltration, characterized in that the blood to be cleaned is exposed to a high-frequency electromagnetic field prior to and/or during contact with the dialyser.

The invention is based on the finding that the bonds between uraemic toxins and plasma proteins are, as a rule, no "true" chemical (covalent) bonds but reversible bonds. These bonds are substantially based on the electrostatic properties of and the interaction between the relevant molecules. It has been found that the strength of said bonds or intensity of said interaction can be reduced according to the invention by applying high-frequency electromagnetic fields. If high-frequency electromagnetic fields are used during dialysis, the amount of protein-bound uraemic toxins can be greatly reduced. In the context of dialysis in everyday clinical practice, the additional use of high-frequency electromagnetic fields serves to increase the percentage of protein-bound uraemic toxins that are released from their protein-bound state. This achieves an improved separation of these substances from the blood of the patient during dialysis. As a result, the relevant uraemic toxins can be dialysed to a greater extent and more effectively.

In the context of the use according to the invention, a dialyser is used for the exchange of substances. Said dialyser senses to remove uraemic toxins as effectively as possible from the blood to be cleaned. In the dialyser, the blood to be cleaned and a liquid that is to be used as a dialysing fluid, the so-called dialysate, are separated from each other by a semipermeable membrane. As a rule, said dialysate flows through the dialyser in a dialysate flow system in a direction contrary to that of the blood flowing in the blood flow system. The exchange of substances between the blood to be cleaned on the one side of the semipermeable membrane of the dialyser and the dialysate on the other takes place through said membrane. The uraemic toxins are transported through the membrane by diffusion or convection. The selectivity of the exchange of substances is determined by the properties of the membrane, e.g. the pore size, on the one hand and by the composition of the dialysate on the other. Suitable dialysers are described in the state of the art, and their use is known to those skilled in the art. Usually, capillary dialysers are used. The dialyser preferably comprises a semipermeable membrane having a size exclusion limit selected from the range from 10,000 to 25,000 Da, preferably from 14,000 to 17,000 Da.

The blood to be cleaned is exposed to a high-frequency electromagnetic field once it is obtained from the patient and before or while or both before and while the blood to be cleaned is in contact with the dialyser or the semipermeable membrane of the dialyser. In a preferred variant of the use according to the invention, the blood to be cleaned is exposed to the high-frequency electromagnetic field when it enters the dialyser. This approach has the advantage that the uraemic toxins are released from their protein-bound state as soon as the blood starts passing through the dialyser, so that the entire capacity of the dialyser is available for the exchange of substances with the dialysate. If the blood to be cleaned is exposed to the high-frequency electromagnetic field while it is in contact with the dialyser, the blood to be cleaned may be exposed to the high-frequency electromagnetic field during the entire passage through the dialyser or only during part of said passage. It is also possible that the blood to be cleaned is exposed to the high-frequency electromagnetic field at several points during its passage through the dialyser.

According to the invention, a high-frequency electromagnetic field is used to break the bonds between plasma proteins and uraemic toxins. Said high-frequency electromagnetic field may have a frequency from 100 kHz to 1 GHz, preferably from 0.5 MHz to 100 MHz, particularly preferred from 1 MHz to 50 MHz, most preferably from 1 MHz to 20 MHz. The blood to be cleaned may be exposed to a high-frequency electromagnetic field whose frequency remains substantially constant over time. Alternatively, the high-frequency electromagnetic field may have a varying frequency, wherein the frequency and/or the field strength may be varied in a regular or irregular manner. In an exemplary embodiment, the blood to be cleaned is exposed to a high-frequency electromagnetic field whose frequency is relatively low at the beginning and is increased over time until a predefined maximum frequency is reached. Alternatively, the blood to be cleaned may also be exposed to a high-frequency electromagnetic field having a high maximum frequency at the beginning which is reduced over time until a predefined minimum frequency is reached. The use of a high-frequency electromagnetic field with varying frequencies serves to improve the effectiveness of breaking the bonds between uraemic toxins and plasma proteins.

To achieve an effective elimination of the bonds between uraemic toxins and plasma proteins, it is advantageous if the high-frequency electromagnetic field is applied to the blood/plasma to be cleaned for a defined period of time, so that atoms of the relevant molecules or the entire molecules can be made to oscillate. To this end, the blood to be cleaned can be exposed to the high-frequency electromagnetic field according to the invention for a time of at least $\frac{1}{10}$ seconds, preferably for a time of at least $\frac{1}{2}$ seconds, particularly preferred for a time of at least one second.

To separate the uraemic toxins from the plasma proteins as effectively as possible, it may be advantageous to use high-frequency electromagnetic fields having a defined electric or magnetic field strength. For example, the high-frequency electromagnetic field used may have an electric field strength of ≤100 V/m, in particular from 0.001 to 100 V/m, preferably from 0.81 to 10 V/m, particularly preferred from 0.1 to 10 V/m. The high-frequency electromagnetic field used may, for example, have a magnetic flux density of ≤100 mT, 2:5 preferably from 0.001 to 100 mT, particularly preferred from 0.01 to 10 mT, ire particular from 0.01 to 2 mT.

Means and methods for generating suitable high-frequency electromagnetic fields are known to those skilled in the art. The high-frequency electromagnetic field used in the method according to the invention may, for example, be generated by means of a high-frequency coil, a high-frequency electrode and/or a high-frequency capacitor.

The present invention also relates to a dialysis machine for carrying out the use according to the invention. A dialysis machine comprises, as a rule, a dialysate flow system, a blood flow system and a dialyser provided for the exchange of substances between the blood to be cleaned of the blood flow system and the dialysate of the dialysate flow system.

The dialysate that is to be used as a dialysing fluid is circulated in the dialysate flow system. The term "dialysate flow system" means a pipe system in which the dialysate, which is first contained in a reservoir, can be moved through the dialyser, e.g. by means of a pump, in such a manner that the dialysing fluid is passed through the dialyser in a direction opposite to that of the blood to be cleaned and on the side of the dialyser membrane facing away from said blood. Once the dialysate has passed through the dialyser, it can be discharged and collected in another container if appropriate. Alternatively, the dialysate can be returned to the dialysate flow system in order to pass through the dialyser again.

The blood to be cleaned is circulated in the blood flow system. The term "blood flow system" means a pipe system in which the blood to be cleaned is obtained from the patient and can be moved through the dialyser, e.g. by means of a pump, in such a manner that the blood to be cleaned is passed through the dialyser in a direction opposite to that of the dialysate and on the side of the semipermeable dialyser membrane facing away from the dialysate. Once it has passed through the dialyser, the cleaned blood is returned to the patient.

In addition, the dialysis machine according to the invention comprises means for carrying out the use according to the invention, in particular means for generating a high-frequency electromagnetic field. Means and methods for generating suitable high-frequency electromagnetic fields are known to those skilled in the art. In order to generate a high-frequency electromagnetic field, the dialysis machine according to the invention may, for example, comprise a high-frequency coil, a high-frequency electrode and/or a high-frequency capacitor.

The means for generating a high-frequency electromagnetic field may be designed and arranged in or on the blood flow system in such a manner that the blood to be cleaned can be exposed to the high-frequency electromagnetic field before, while or both before and while the blood to be cleaned is in contact with the dialyser or with the semipermeable membrane of the dialyser.

The dialysis machine according to the invention may, in addition, comprise a regulating and/or control unit. This regulating and/or control unit may be designed such that it serves to regulate and/or control parameters of the high-frequency electromagnetic field. Such parameters may include, for example, the frequency, the electric field strength, the magnetic flux density and/or the duration of the high-frequency electromagnetic field. To this end, the regulating and/or control unit may comprise an input unit, a computing unit and, if appropriate, a memory unit, by means of which a user of the dialysis machine can regulate and/or control the parameters of the high-frequency electromagnetic field. In a preferred embodiment, the regulating and/or control unit is designed such that a user can also use it to regulate and/or control parameters of the dialysate flow system and/or the blood flow system, such as the flow rate of the blood to be cleaned and/or of the dialysing fluid and/or the dialysate.

The invention will now be explained in more detail with reference to exemplary embodiments.

FIGURES:

FIG. 1 shows a schematic view of a dialysis machine according to the invention.

Figure 2:
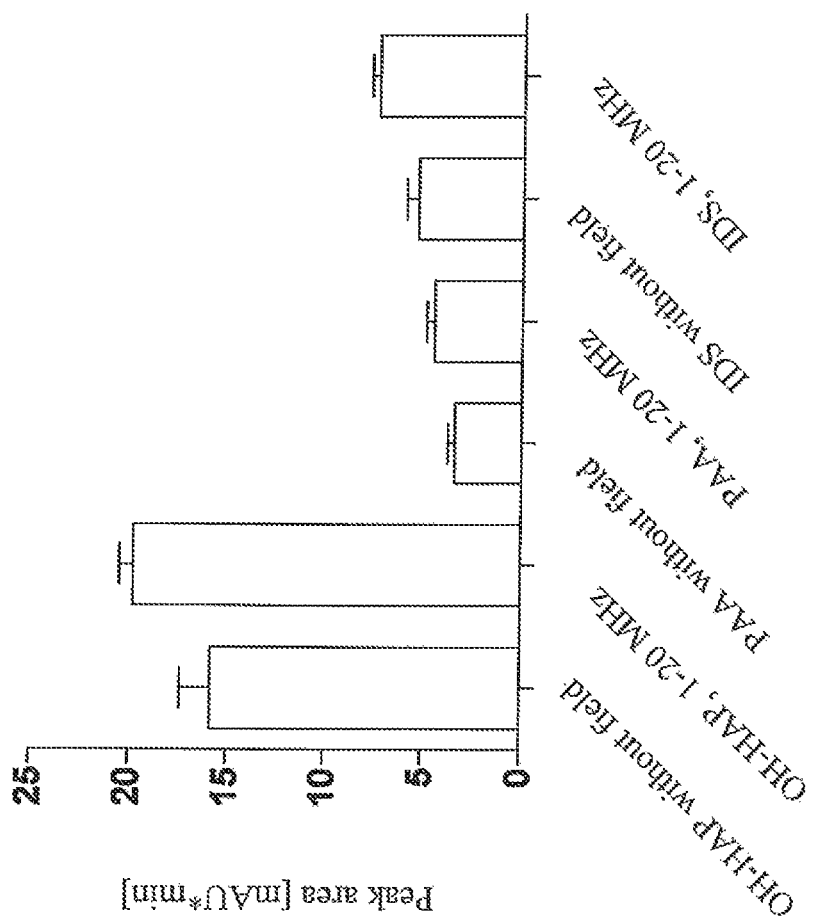

FIG. 2 shows the amount of uraemic toxins (rel. peak areas) in the filtrate in the presence and absence of a high-frequency field (OH-HPA=p-hydroxyhippuric acid; PAA=phenylacetic acid; IDS=indoxyl sulphate).

Figure 3:
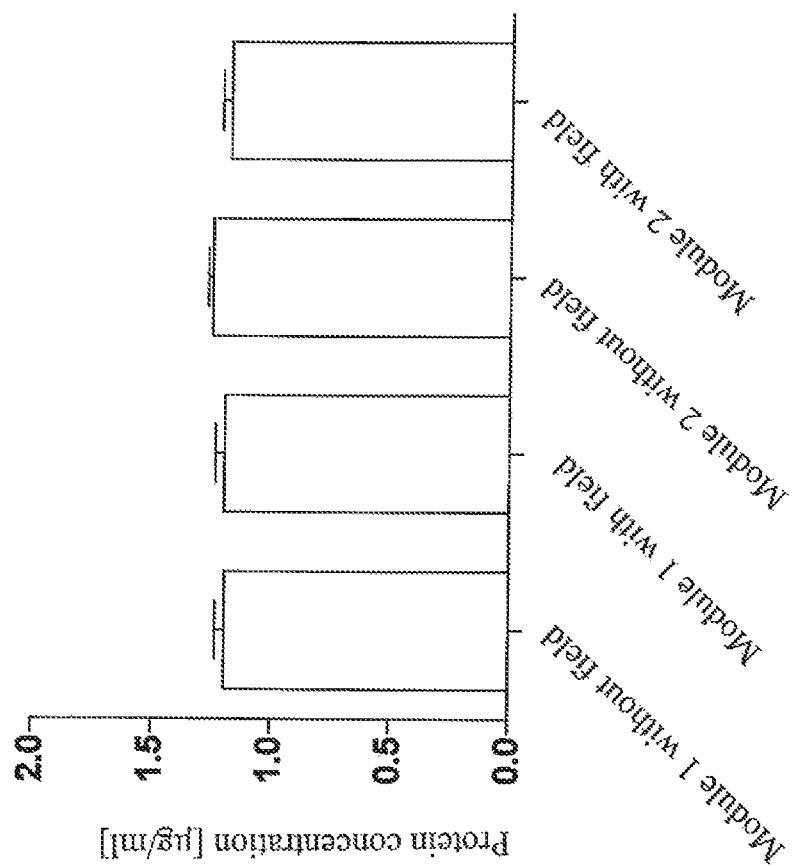

FIG. 3 shows the protein concentrations in the filtrate in the presence and absence of an HF field for two structurally identical modules (no significant difference).

EXAMPLES

Example 1

Description of Dialysis Machine According to the Invention

FIG. 1 shows a schematic view of a dialysis machine 1 according to the invention, which is suitable for carrying out the use according to the invention. The dialysis machine 1 comprises a dialysate flow system 2, a blood flow system 5 and a dialyser 4, which are interconnected in such a manner that blood, which circulates in the blood flow system 5 and is to be cleaned in the dialyser 4, and dialysate, which circulates in the dialysate flow system, can be passed next to each other in opposite directions on different sides of the semipermeable membrane, so that an exchange of substances between the blood and the dialysate is possible through the semipermeable membrane of the dialyser 4. A pump 6 may be provided to transport blood through the blood flow system 5 in a defined direction. A dialysate pump 3 may be provided to transport dialysate through the dialysate flow system in a defined direction. The dialyser 4 may, for example, be designed as a capillary dialyser comprising a semipermeable membrane whose size exclusion limit ranges from 10,000 Da to 20,000 Da. In general, the dialysis machine 1 according to the invention may be assembled using known, conventional dialysis technology, and it can generally be based on all known dialysis machines or dialysis devices. In addition, the dialysis machine 1 comprises means 7 for generating a high-frequency electromagnetic field. Such means may, for example, be a high-frequency coil, a high-frequency electrode and/or a high-frequency capacitor. The dialysis machine 1 according to the invention may, in addition, comprise a regulating and/or control unit 8. This regulating and/or control unit 8 may be designed and connected to the means 7 in such a manner that it serves to regulate and/or control parameters of the means 7 for generating a high-frequency electromagnetic field. Such parameters may include, for example, the electric frequency, the electric field strength, the magnetic flux density and/or the duration of the high-frequency electromagnetic field. To this end, the regulating and/or control unit 8 may comprise an input unit, a computing unit and a memory unit, by means of which the user of the dialysis machine 1 can regulate and/or control the parameters of the high-frequency electromagnetic field. In a preferred embodiment, the regulating and/or control unit t is designed such that a user can also use it to regulate and/or control parameters of the dialysate flow system 2 and/or the blood flow system 5, such as the flow rates of the blood to be cleaned and/or of the dialysate.

Example 2

Proof of Effect

The effect of high-frequency electromagnetic fields on the protein-bound portion of uraemic toxins was studied by means of in vitro test series. For this purpose, a dialysis module was assembled by embedding loops formed of conventional haemofiltration capillaries in a syringe barrel by means of silicone. An aqueous albumin solution containing the uraemic toxins phenylacetic acid, p-hydroxyhippuric acid and indoxyl sulphate was introduced in the module. A syringe pump was used to filter this solution by means of the dialysis module for 10 min. Then, a high-frequency electromagnetic field was induced in the solution using a high-frequency electrode (HF electrode). The electromagnetic field is incremented by means of a high-frequency voltage source over 10 min, from 1 to 20 MHz in 1 MHz increments. In the resulting filtrates, the concentrations of the uraemic toxins phenylacetic acid, p-hydroxy-hippuric acid and indoxyl sulphate, which had been added to the artificial plasma, were determined. The effect of the HF field on the bonds between proteins and uraemic toxins could be evaluated by comparing the concentrations of the uraemic toxins in the resulting filtrates.

The quantitative determination of the concentrations of the uraemic toxins in the resulting filtrates showed that high-frequency electromagnetic fields significantly increase the filtration rates of protein-bound uraemic toxins (FIG. 2). To check whether high-frequency electromagnetic fields damage the dialysis membranes, the protein concentration in the filtrate was determined by means of the Bradford protein assay. The results show that no significant changes of the protein concentration can be detected in dialysis modules that are exposed to high-frequency electromagnetic fields, compared to those that are not (FIG. 3). Based on this data macroscopic damage to the membrane can be excluded.

LIST OF REFERENCE NUMERALS

1 Dialysis machine
2 Dialysate flow system
3 Dialysate pump
4 Dialyser
5 Blood flow system
6 Pump
7 Means for generating a high-frequency electromagnetic field
8 Regulating and/or control unit

The invention claimed is:

1. A method of removing protein-bound toxins from the blood of a patient comprising:
   providing a dialysis machine including
   a dialysate flow system,
   a blood flow system,
   a dialyser, and
   a device configured to generate a high-frequency electromagnetic field;
   applying the high-frequency electromagnetic field to the blood flow system prior to and/or along the dialyser in a manner to release uraemic toxins from protein-bound states during dialysis, such that the a percentage of uraemic toxins that are released from their protein-bound states is increased versus non-application of the high-frequency electromagnetic field during dialysis; and dialyzing the released uraemic toxins from the blood flow system into the dialysate flow system.

2. The method of claim 1, wherein applying the high-frequency electromagnetic field in the percentage increasing manner includes applying the high-frequency electromagnetic field at a frequency of 1 MHz to 20 MHz and at an electric field strength of no more than 100 V/m.

3. The method of claim 1, wherein applying the high-frequency electromagnetic field in the percentage increasing manner includes applying the high-frequency electromagnetic field at a frequency that is constant over time.

4. The method of claim 1, wherein applying the high-frequency electromagnetic field in the percentage increasing manner includes applying the high-frequency electromagnetic field at a frequency that varies in a regular or irregular manner.

5. The method of claim 1, wherein applying the high-frequency electromagnetic field in the percentage increasing manner includes applying the high-frequency electromagnetic field to blood in the blood flow system prior to and/or along the dialyser for at least a second.

6. The method of claim 1, wherein applying the high-frequency electromagnetic field in the percentage increasing manner includes applying the high-frequency electromagnetic field having an electric field strength from 0.1 to 10 V/m.

7. The method of claim 1, wherein applying the high-frequency electromagnetic field in the percentage increasing manner includes the high-frequency electromagnetic field having an electric field density of ≤100 mT.

8. The method of claim 1, wherein dialyzing the released uraemic toxins from the blood flow system into the dialysate flow system includes circulating blood through the blood flow system, while circulating dialysate through the dialysate flow system, and wherein the dialyzing occurs while applying the high-frequency electromagnetic field to the blood flow system.

9. The method of claim 8, which includes circulating blood through the blood flow system and dialysate through the dialysate flow system in opposite directions.

10. The method of claim 1, wherein dialyzing the released uraemic toxins from the blood flow system into the dialysate flow system includes passing the released uraemic toxins across at least one semipermeable membrane of the dialyser.

11. A method for treating a patient experiencing renal failure, the method comprising:
providing a dialyser configured to receive blood from the patient and dialysate on opposite sides of a semipermeable membrane;
generating a high-frequency electromagnetic field via a high-frequency coil, a high-frequency electrode or a high-frequency capacitor;
applying the high-frequency electromagnetic field to the blood in a manner so as to break bonds between uraemic toxins and plasma proteins, causing the uraemic toxins to be freed from the plasma proteins; and
removing the freed uraemic toxins from the blood, through the semipermeable membrane and into the dialysate while flowing blood and dialysate through the dialyser.

12. The method of claim 11, wherein generating the high-frequency electromagnetic field includes generating the high-frequency electromagnetic field at a frequency of 1 MHz to 20 MHz and at an electric field strength of no more than 100 V/m.

13. The method of claim 11, wherein generating the high-frequency electromagnetic field includes generating the high-frequency electromagnetic field at a frequency that is constant over time.

14. The method of claim 11, wherein generating the high-frequency electromagnetic field includes generating the high-frequency electromagnetic field at a frequency that varies in a regular or irregular manner.

15. The method of claim 11, wherein generating the high-frequency electromagnetic field includes the high-frequency electromagnetic field having an electric field strength from 0.1 to 10 V/m.

16. The method of claim 11, wherein generating the high-frequency electromagnetic field includes generating the high-frequency electromagnetic field having an electric field density of ≤100 mT.

17. The method of claim 11, wherein applying the high-frequency electromagnetic field in the bond breaking manner includes applying the high-frequency electromagnetic field to blood in the blood flow system for at least a second.

18. The method of claim 11, wherein applying the high-frequency electromagnetic field in the bond breaking manner includes applying the high-frequency electromagnetic field prior to and/or along the dialyser.

19. The method of claim 1, wherein removing the freed uraemic toxins from the blood includes flowing blood and dialysate through the dialyser in opposite directions, while applying the high-frequency electromagnetic field to the blood.

20. The method of claim 19, wherein removing the freed uraemic toxins from the blood includes collecting dialysate containing the freed uraemic toxins in a container.

* * * * *